(12) United States Patent
Larsen

(10) Patent No.: US 8,475,438 B2
(45) Date of Patent: Jul. 2, 2013

(54) METHOD AND APPARATUS FOR NON- OR MINIMALLY DISRUPTIVE PHOTOMANIPULATION OF AN EYE

(76) Inventor: Lars Michael Larsen, Charlottenlund (DK)

( * ) Notice: Subject to any disclaimer, the term of this patent is extended or adjusted under 35 U.S.C. 154(b) by 1028 days.

(21) Appl. No.: 12/514,095

(22) PCT Filed: Nov. 12, 2007

(86) PCT No.: PCT/DK2007/000495
§ 371 (c)(1),
(2), (4) Date: Jul. 8, 2009

(87) PCT Pub. No.: WO2008/055506
PCT Pub. Date: May 15, 2008

(65) Prior Publication Data
US 2010/0292676 A1    Nov. 18, 2010

(30) Foreign Application Priority Data
Nov. 10, 2006 (DK) .................................. 2006 01468

(51) Int. Cl.
*A61B 18/18* (2006.01)
(52) U.S. Cl.
USPC .................................. 606/4; 606/11; 607/89
(58) Field of Classification Search
USPC ........................ 606/4–7, 10–12; 607/88, 89
See application file for complete search history.

(56) References Cited

U.S. PATENT DOCUMENTS

| | | |
|---|---|---|
| 4,582,405 A | 4/1986 | Muller et al. |
| 4,644,948 A * | 2/1987 | Lang et al. .......................... 606/4 |
| 5,057,098 A | 10/1991 | Zelman |
| 5,403,307 A | 4/1995 | Zelman |

(Continued)

FOREIGN PATENT DOCUMENTS

| | | |
|---|---|---|
| DE | 19718139 A1 | 11/1998 |
| EP | 0412789 | 2/1991 |

(Continued)

OTHER PUBLICATIONS

Lehman, et al: "Inhibitors of advanced glycation and product-associated protein cross-linking", Biochimica et Biophysica Acta 1535, 2001, pp. 110-119.
Lerman, et al: "Spectroscopic evaluation and classification of the normal, aging, and cataractous lens". Opthal res. 8, 1976 pp. 335-353.

(Continued)

*Primary Examiner* — Darryl J Collins
(74) *Attorney, Agent, or Firm* — Gifford, Krass, Sprinkle, Anderson & Citkowski, P.C.

(57) ABSTRACT

The invention related to a method and a system for non- or minimally disruptive photomanipulation of the lens and/or its constituents collectively or selectively of an animal or human eye, comprising focusing a treatment laser beam into a selected part of the lens and/or its constituents collectively or selectively where treatment is intended to occur, pulsing of said treatment laser beam, scanning the beam over at least a part of the lens, measuring one or more types of radiation from the said selected part and utilizing this measurement to decide to stop the said treatment laser beam or to adjust at least one of the parameters: focus, intensity, wavelength, pulse length, repetition frequency, pulse train length, scan velocity, size of scanned volume, scan repetitions, and scan pattern of said treatment laser beam.

50 Claims, 5 Drawing Sheets

U.S. PATENT DOCUMENTS

| | | |
|---|---|---|
| 5,843,071 A | 12/1998 | Bath |
| 6,066,127 A | 5/2000 | Abe |
| 6,280,435 B1 | 8/2001 | Odrich et al. |
| 6,322,554 B1 | 11/2001 | Tomita |
| 6,322,556 B1 | 11/2001 | Gwon et al. |
| 6,478,792 B1 | 11/2002 | Hansel |
| 6,726,679 B1 | 4/2004 | Dick et al. |
| 7,686,450 B2 | 3/2010 | Heiberger |
| 2008/0177256 A1* | 7/2008 | Loesel et al. ............ 606/4 |

FOREIGN PATENT DOCUMENTS

| | | |
|---|---|---|
| EP | 1231496 | 8/2002 |
| EP | 1396244 | 3/2004 |
| JP | 2002058695 A | 2/2002 |
| JP | 2004113322 A | 4/2004 |
| JP | 2008528141 A | 7/2008 |
| RU | 2243754 | 2/2005 |
| SU | 1837855 | 8/1993 |
| WO | WO-9308677 | 5/1993 |
| WO | WO-9325166 | 12/1993 |
| WO | WO-0113838 | 3/2001 |
| WO | 2005007002 A1 | 1/2005 |
| WO | 2006050424 A2 | 5/2006 |
| WO | 2006076653 A2 | 7/2006 |
| WO | 2006081814 A1 | 8/2006 |

OTHER PUBLICATIONS

Nakamura et al: "Acid-stable fluorescent advanced glycation and products: vesperlysines A, B, and C are formed as crosslinked products in the Malliard reaction between lysine or proteins with glucose"; Biochem Biophys Res. Commun. Mar. 6, 1997 232(1) pp. 227-230.

Orthwerth et al: "Ascorbic acid glycation of lens proteins produces UVA sensitizers similar to those in human lens", Photochem Photobiol, Sep. 1995, 63(3) pp. 454-452.

Ortwerth et al: "Ascorbic acid glycation: the reactions of L-threose in lens tissue", Exp Eye Res, Jun. 1994, 58(6) pp. 665-674.

Ortwerth et al: "Studies on singlet oxygen formation and UVA light-mediated photobleaching of the yellow chromophores in human lenses", Exp. Eye Res., 2002 74, pp. 217-229.

Sander et al: "Photochemical bleaching of fluorescent glycosylation products", Inc. Opthalml, 1B, 1995 pp. 195-198.

Tessier et al. "Structure and mechanism of formation of human lens fluorophore LM-1". The Journal of Biological Chemistry. vol. 274, No. 30, Jul. 23, 1998 pp. 20796-20804.

Zhou et al: "Characterization of a tunable optical parametric oscillator laser system for multielement flame laser excited atomic fluorescence spectrometry of cobalt, copper, lead, manganese, and thallium in buffalo river sediment", Anal. Chem. 69 1997, pp. 490-499.

* cited by examiner

METHOD AND APPARATUS FOR NON- OR MINIMALLY DISRUPTIVE PHOTOMANIPULATION OF AN EYE

CROSS-REFERENCE TO RELATED APPLICATIONS

This application is the U.S. National Phase of PCT/DK2007/000495 filed Nov. 12, 2007, which claims priority of Danish Patent Application PA 2006 01468 filed Nov. 10, 2006.

All patent and non-patent references cited in the application, or in the present application, are also hereby incorporated by reference in their entirety.

FIELD OF INVENTION

The present invention relates to a method for non- or minimally disruptive photomanipulation of the lens and/or its constituents, collectively or selectively, of an animal or human eye.

BACKGROUND OF INVENTION

Opacities in the eye are primarily caused by cataract which is globally the leading cause of blindness, whereas hardening of the lens is primarily related to presbyopia. Presbyopia is defined as a decrease in accommodative amplitude of the eye resulting in an inability to correctly focus light on the retina from objects at variable distance. This is usually noticed by emmetropic subjects (persons who do not need spectacle or contact lens correction for distance vision) between age 40-50 as inability to see close objects clearly.

When an human is born, the lens is transparent even to ultraviolet and the dense protein content of the lens forms a well-organised, elastical and flexibles substance. From the age of 10 years, progressive yellowing begins to change the lens, concurrently or in close relation to the loss of accommodative amplitude. Ultimately, in the $7^{th}$ or $8^{th}$ decade of life, a large proportion of subjects will have developed visual impairment secondary to cataract, i.e. opacification of the lens.

On a global level, thousands of people are blinded each year by cataract and at present the only cure is removal of the lens by surgery. For many people surgery is not an option because of lack of access to modern standards of surgical treatment. Even in industrialized countries the burden of treatment creates significant problems for the health care systems. Thus, an instrument for restoration of visual function (accommodative amplitude and clarity) by treatment of the lens, preferably non-invasive, will be of significant value for the prevention and treatment of visual dysfunction.

The yellow coloration of the lens is believed to be caused by the formation of covalent cross-links and aggregation of degraded proteins in the lens. Molecular cross-links and other types of degradation disrupt the optical and mechanical properties of the lens. The fluorescence of cyclic molecular components of the cross-links is early evidence of this process.

The application of laser light for photomanipulation of the eye is well known in the field of opthalmology. In this context laser light is understood as light which is sufficiently monochromatic to allow sufficient focus. One example of the application of laser light is U.S. Pat. No. 6,322,556 where laser light is applied to ablate and thereby remove small portions of the lens with the purpose of correcting vision. A different application is described in U.S. Pat. No. 6,726,679 where laser light is applied to dissolve opacities and/or hardenings of an unopened eye. However this method has several drawbacks. Firstly, with the eye closed it is not possible to determine exactly where in the lens the eye is being treated, which in turn may result in damages as the same position may mistakenly be treated several times. Secondly, the correct dose of laser light applied to a position within the eyes to achieve a significant clinical result is highly individual and may vary with the position in the lens. With set values of the laser this may result in ineffective under-treatment or damaging over-treatment. Damages may occur due to local evaporation of the constituents in the lens resulting in gas blisters (cavitation bubbles). Such blisters are considered unavoidable and in some instances preferable in U.S. Pat. No. 6,726,679, however their appearance and collapse may induce significant mechanical stress on the lens and/or surrounding tissue, so the formation of gas blisters should be avoided, or be avoidable, in a manner that can be controlled by the treating physician or therapist or an automated therapeutic instrument. On the other hand, when using methods such as described in U.S. Pat. No. 6,726,679 it is difficult to adjust the amount of energy, so as to obtain sufficient treatment effect while avoiding or minimizing undesired effects, such as gas blisters or photodamage of the cornea or the living layers of the lens. In spite of these risks, there is no doubt that the non-invasive reduction or removal of opacity and hardenings in the lens is an important clinical goal. It is therefore an object of the present invention to provide a method and apparatus for non-invasive photomanipulation of the lens and/or its constituents, collectively or selectively, while ensuring efficiency and/or ensuring that only the minimally- or non-disruptive amount of photonic energy is transmitted to the eye.

SUMMARY OF INVENTION

The present invention relates to a method and system for photobleaching or other non-disruptive or minimally disruptive photomanipulation of the lens of the eye of the animal or human eye and/or its constituent components, selectively or collectively. The aim is to change the optical or mechanical properties of lens in such a way as to enhance its optical transmittance and/or increase its accommodative range or ability to undergo deformation during the physiological process of accommodation, i.e. the dynamic adjustment of the focal length of the eye. The desired effect or effects being achieved by inducing bleaching of chromophores, resolubilisation of precipitated matter with abnormal refractive or light scattering properties, disjunction of molecules that have undergone denaturation that involving cross-linking, alteration of physical chemistry characteristics of lens constituents by disruption of covalent bonds. This is done under preferably continuous feed-back control of the changes in optical characteristics of the lens so as to avoid or minimize damage resulting from cavitations or other disruptive effects that lead to whole-cell damage, opacification, stiffening or other undesirable effect in the lens.

In particular is realized that optimum photomanipulation, while ensuring that undesired effects are avoided or minimized, is obtainable by a method for non- or minimally disruptive photomanipulation of the lens and/or its constituents collectively or selectively of an animal or human eye, comprising:
  a) focusing a treatment laser beam into a selected part of the lens and/or its constituents collectively or selectively where treatment is intended to occur;
  b) pulsing of said treatment laser beam;

c) measuring one or more types of radiation from the said selected part and utilizing this measurement to decide to stop the said treatment laser beam or to adjust at least one of the parameters: focus, intensity, wavelength, pulse length, repetition frequency, and pulse train length of said treatment laser beam, whereby the photomanipulation is effectively monitored allowing for an accurate and optimum application of photo energy.

Furthermore, in a second aspect of the invention relates to a system for non- or minimally disruptive photomanipulation of the lens and/or its constituents collectively or selectively of an animal or human eye, comprising:

d) a treatment laser system for emitting at least one treatment laser beam;
e) focusing means for focusing said treatment laser beam into a selected part of the lens and/or its constituents collectively or selectively where treatment is intended to occur;
f) means for pulsing of said treatment laser beam;
g) means for measuring one or more types of radiation from the said selected part;
h) means for processing the said one or more type of radiation from the said selected part;
i) means for adjusting, based on at least part of the output of the means for processing, at least one of the parameters for the said treatment laser beam: focus, intensity, wavelength, pulse length, repetition frequency, and pulse train length of said treatment laser beam.

In a third aspect the invention relates to a system and method a method of mechanically immobilizing the living eye, wholly or partly, during treatment, by mechanical contact with the surface of the eye or by mechanical contact to a contact lens mounted on the eye, as well as a system of mechanically immobilizing the living eye, wholly or partly, during treatment, comprising means for mechanical contact with the surface of the eye and/or means for mechanical contact to a contact lens mounted on the said eye.

In a fourth aspect the invention relates to a method of tracking the movement of the eye by imaging of the eye on at least one light detector, as well as a system of tracking the movement of the eye comprising means for imaging of the eye on at least one light detector.

In a fifth aspect the invention relates to a method for monitoring the orientation of an eye in space by simultaneously monitoring the surface or anterior part of the eye and the fundus (posterior inside of the eye) and calculating the orientation of the eye in space as well as a system for monitoring the orientation of an eye in space comprising means for monitoring the surface or anterior part of the eye and means for monitoring the fundus and means for calculating the orientation of the eye in space In a sixth aspect the invention relates to a method for conditioning the eye prior to treatment, during treatment, prior to assessment or during assessment by applying at least on of the following: heat, cold and magnetic field as well as a system for conditioning the eye comprising means for applying at least on of the following: heat, cold and magnetic field.

In a seventh aspect the invention relates to a method of treating a person or animal in need of treatment for cataract, pre-cataract or presbyopia by non- or minimally disruptive photomanipulation of the lens and/or its constituents collectively or selectively of an animal or human eye, comprising:

j) focusing a treatment laser beam into a selected part of the lens and/or its constituents collectively or selectively where treatment is intended to occur;
k) pulsing of said treatment laser beam;
l) measuring one or more types of radiation from the said selected part and utilizing this measurement to decide to stop the said treatment laser beam or to adjust at least one of the parameters: focus, intensity, wavelength, pulse length, repetition frequency, and pulse train length of said treatment laser beam.

thereby photobleaching said cataract, pre-cataract or presbyopia and thus treating the disease. Furthermore, the invention relates to a system for treating a person or animal in need of treatment for cataract, pre-cataract or presbyopia by non- or minimally disruptive photomanipulation of the lens and/or its constituents collectively or selectively of an animal or human eye, comprising:

m) means for focusing a treatment laser beam into a selected part of the said lens and/or its constituents collectively or selectively where treatment is intended to occur;
n) means for pulsing of said treatment laser beam;
o) means for measuring one or more types of radiation from the said selected part;
p) means for processing the said one or more type of radiation from the said selected part;
q) means for adjusting at least one of the parameters for the said treatment laser beam: focus, intensity, wavelength, pulse length, repetition frequency, and pulse train length of said treatment laser beam.

Thereby optimally photobleaching said cataract, pre-cataract or presbyopia and thus treating the disease.

In an eight aspect, the invention relates to a method for non-invasive treatment of the lens and/or its constituents collectively or selectively of an animal or human eye, comprising r) focusing a treatment laser beam into a selected part of the lens and/or its constituents collectively or selectively where treatment is intended to occur;
s) pulsing of said treatment laser beam;
t) scanning the treatment laser beam over the lens or at least parts thereof with a constant or varying velocity;
u) measuring one or more types of radiation from the said selected part and utilizing this measurement to decide to stop the said treatment laser beam or to adjust at least one of the parameters: focus, intensity, wavelength, pulse length, repetition frequency, pulse train length, scan velocity, size of scanned volume, scan repetitions, and scan pattern of said treatment laser beam;

In a ninth aspect, the invention relates to a system for non-invasive treatment of the lens and/or its constituents collectively or selectively of an animal or human eye, comprising v) means for focusing a treatment laser beam into a selected part of the lens and/or its constituents collectively or selectively where treatment is intended to occur;
w) means for pulsing of said treatment laser beam;
x) means for scanning the treatment laser beam over the lens or at least parts thereof with a constant or varying velocity;
y) means for measuring one or more types of radiation from the said selected part and means for utilizing this measurement to decide to stop the said treatment laser beam or to adjust at least one of the parameters: focus, intensity, wavelength, pulse length, repetition frequency, pulse train length, scan velocity, size of scanned volume, scan repetitions, and scan pattern of said treatment laser beam;

In a tenth aspect, the invention provides a method and a system for simultaneous use of multiple probing beams entering the eye, each forming its own separate focus or target volume where a desired light-elicited response takes place, such a response being for instance fluorescence or another emission that enables control of target position, focus, and intensity in the lens.

In an eleventh aspect, the invention provides a method and a system for simultaneous use of multiple treatment beams entering the eye, each forming its own separate focus or target volume where a desired light-elicited chemical reaction or structural alteration change takes place, while avoiding side-effects that would follow from having the total energy delivered to the eye concentrated in a single focus.

DESCRIPTION OF DRAWINGS

In the following, the invention is described in more detail with reference to the accompanying drawings, in which.

DETAILED DESCRIPTION OF THE INVENTION

Feedback

Figure 1:
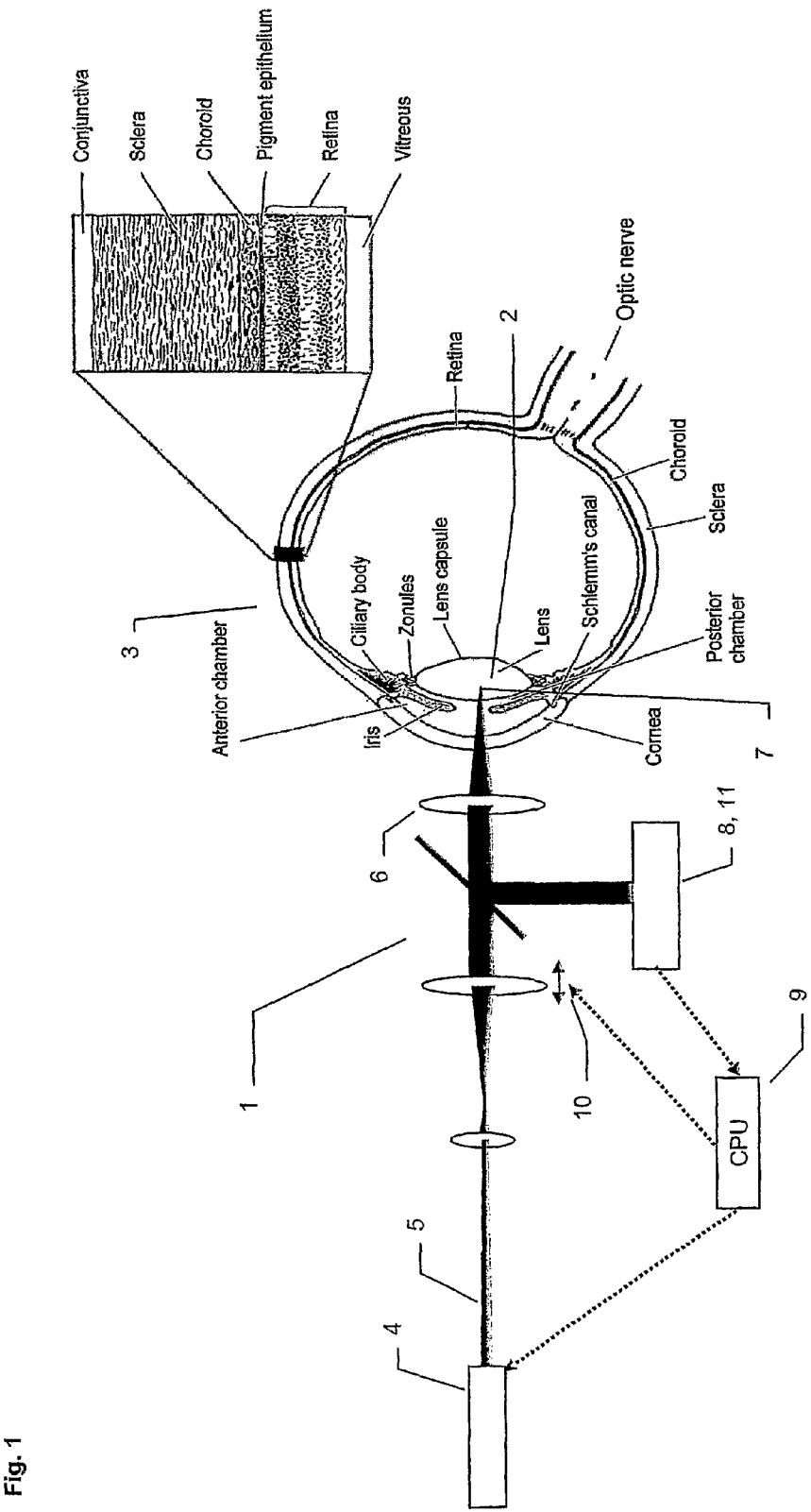
FIG. 1 shows a schematic overview of a system according to the invention.

Emission of radiation, such as autofluorescence, emitted from the crosslinked proteins can be used to monitor photochemical reactions. It is preferred that at least one of said types of radiation arises due to said treatment laser beam. Thereby, the characteristics of said radiation, the analysis of which is used to adjust the treatment laser beam will depend directly on the said treatment laser beam. However, it may also be advantageous the at least one of said types of radiation arises due to a secondary source of radiation, such as a laser. Thereby, the said selected part may e.g. be manipulated at one wavelength but probed for characterizing radiation using a different wavelength.

A preferred embodiment of the method according to the invention further comprises an initialization phase, where non-manipulative intensity is directed to the said selected part and one or more types of radiation, caused by the interaction between the said part and the said non-manipulative intensity, are measured and utilizing this measurement to decide not to photomanipulate said selected part or decide to proceed with photomanipulation. Thereby, the suitability of the said selected part for photomanipulation may be assessed. Furthermore, it is preferred that the said initialization phase is further utilized to adjust at least one of the following: focus, intensity, wavelength, pulse length, repetition frequency, pulse train length, scan velocity, size of scanned volume, scan repetitions, and scan pattern of said treatment laser beam. Thereby the setting of the parameters for the photomanipulation are pre-optimized so that the probability of undesired effect arising from the first photomanipulation is minimized.

A second preferred embodiment of the method according to the invention comprises an assessment phase after application of the said treatment laser beam where non-manipulative intensity is directed to the said selected part and measuring one or more types of radiation caused by the interaction between the said part and the said non-manipulative intensity and utilizing this measurement to decide to stop further treatment of said part or to resume treatment with or without adjustment of at least one of the following: focus, intensity, wavelength, pulse length, repetition frequency, pulse train length, scan velocity, size of scanned volume, scan repetitions, and scan pattern of said treatment laser beam. Thereby, it may be verified if sufficient photomanipulation has occurred or if it has not the results of the said assessment may be used to optimize further photomanipulation.

In a preferred method according to the invention the said measurement involve determining the optical signature of the said selected part comprising at least one of the following: transient characteristics arising as an effect of the treatment pulse or any characteristic that can be recorded using steady-state or time-resolved spectroscopy (such as a change in color and absorption), Raman spectroscopy (such as a change in Stoke's shift and Raman scatter intensity), photon-correlation spectroscopy (such as a change in apparent molecular weight, rigidity, and composition), fluorescence spectroscopy (a reduction, increase, spectral shift or other change in lens fluorescence) and/or phosphorescence spectroscopy (a reduction, increase, spectral shift or other change in lens phosphorence).

It is furthermore also preferred that the said measurement involves detection of acoustic effects recorded using non-contact sensor(s) and/or an acoustic sensor placed in direct contact or indirect contact with the eye or adjacent tissue. Non-contact acoustic sensors are well-known in the prior art such a microphones or laser interferometry of laser light reflected off a surface.

Acoustic effects in conjunction with photomanipulation of the lens arise from the forming and especially the collapse of gas blisters and from other types of interaction between light and tissue. Accordingly, including the said acoustic sensor thereby provide for a primary detection of the formation of gas blisters forming as a result of the photomanipulation. With a direct detection it is then possible to positively verify whether or not gas blistering has taken place, and/or to stop further photomanipulation if it does.

In a most preferred method according to the invention the said measurement, analysis and adjustment form a feed-back loop, so the said steps of measurement, analysis and adjustment occur substantially continuously. It furthermore preferred that the said feed-back loop operates substantially in real-time. It is preferred that the said measurement, processing of resulting data, said adjustment(s), and renewed photomanipulation of the said selected part occurs at least within substantially 0.1 second or a shorter time period which is substantially smaller than the spontaneous movements of the eyes (saccades) and preferably shorter than 0.01 second. Within a response time of this order micro movements of the eye may be ignored so that the site from which said radiation is measured corresponds to the site subsequently irradiated.

Adaptive Optics

It is preferred that the treatment laser beam and/or any secondary source of radiation is focused using adaptive optics. Adaptive optics were initially applied in the field of astronomy where distortion of the light field from a distant star caused by the earth atmosphere are removed by adapting the shape of a deformable mirror to the incoming light field. Commonly a so-called guide star is used, which is created by a powerful laser beam reflecting off the outer atmosphere. The deformable mirror is then adjusted until the image of the guide star is clear. In the context of opthalmology, adaptive optics may be applied to compensate for aberrations due to imperfections in the eye tissue, so that the focus of the said treatment laser beam is optimized. It is preferable that the said adaptive optics further comprises the use of a deformable mirror.

Furthermore, it is preferred that the said adaptive optics further comprises the use of a Hartmann-Schack sensor well known from astronomy and opthalmology, ophthalmic applications including the mapping of optical aberrations of the eye prior to and after custom-ablation of the cornea, as currently conducted using excimer laser tissue evaporation. While single-shot adjustment using adaptive optics is possible it may for some applications be preferable that the adaptive optics form a feedback loop where adjustment and measurement of the result is an iterative process. The adaptive optics may be guided by a light sources dedicated to this purpose but it is preferable guided by reflection or other radiation caused by the said treatment laser beam or a said secondary source of radiation.

Radiation Types

In one version of the method according to the invention, the said radiation comprises at least one of the following: fluorescence (detection of broad-band emission of light from the target, at longer wavelength than that of the incoming light), scatter (detection of light emitted from the target at the wavelength of the incoming light), Raman scatter (detection of narrow-band emission of light from the target, at longer or shorter wavelength than that of the incoming light), reflection (specular reflection of the incoming light), phosphorescence (detection of broad-band emission of light from the target, at longer wavelength than that of the incoming light and with a delay of more than 100 nanoseconds), and bremsstrahlung (detection of broad-band emission of light from the target, at both longer and shorter wavelengths than that of the incoming light). Specifically, it may be useful to measure the spectral distribution of the said radiation and thereby utilizing that the spectral radiation is often specific to its molecular origin. Similarly, different time constants, such as relaxation time, may reveal properties of the treatment site. In one embodiment of the invention it is therefore preferred to analyse the measurement of said radiation by temporally resolved analysis.

Goal Related Feedback

In the above described feedback system one or more of several physical goals may be considered in the programming of the feedback system. Accordingly, the feedback system may be programmed to observe specific physical properties and adjust the laser and/or the decision to progress or stop the treatment based on this property. In a preferred embodiment of the invention, such monitoring may be performed by the following steps a) photomanipulating said selected part
b) detection radiation from the said selected part
c) gradually increasing energy of said photomanipulation
d) registering when said radiation is below a defined threshold.

Similarly, in another preferred embodiment of the invention the efficiency of the treatment is investigated by measurement of radiation due to a non-manipulative intensity directed to the said selected part. Finally, such investigation of the efficiency may be performed or supplemented by comparing values of said radiation obtained prior to treatment with the data obtained from said verification In general the goal of the feedback system may be to have said radiation increase, decrease, appear, disappear or have a suitable level. Among the preferred goals of the adjustment of the treatment laser according to the present are adjustment to obtain bleaching, color change, deaggregation of lens components, depolymerization of lens proteins or other constituents of the lens, or resolubilization of lens proteins or other constituents of the lens. This is preferably carried out while avoiding or minimizing cavitation, mechanical effects, acoustic effects, and/or thermal effects on molecules, components, or cells that do not form a target for treatment or are outside said selected area. In the effort to avoid the said event the system may monitor the same or other radiation as the radiation(s) used to determine achievement of the said goal.

Among other preferred goals of the adjustment according to the invention are adjusting the treatment laser beam to obtain molecular cleavage of specific larger molecules or macromolecular adducts, for instance lens proteins or lens protein cross-links, without damage to healthy lens proteins, cell membranes or other healthy components of the lens, and further avoiding or minimizing cavitation, mechanical effects, acoustic effects, and/or thermal effects on molecules, components, or cells that do not form a target for treatment or are outside said selected area. More specifically said radiation may be fluorescence and the system adjusts to simultaneously minimizing or preventing an increase in scattering.

Multi-Photon Effect

Photonic excitation of specific molecular constituents of the human eye using blue light or ultraviolet is problematic because the energetic photons cause damage to the cornea and the living layers of the lens. Additional problems include retinotoxicity and poor penetration of cataractous lenses. A method of circumventing this problem is to use multiphoton excitation. Two-photon excitation achieves specific electronic excitation by laser light with a high intensity and half the wavelength required to induce the desired effect by means of a single photon. The high intensity of the light increases the probability of exciting the flouresence by a two-step process, where the molecule the molecule is first excited to a virtual level by the first photon and subsequently by another photon that strikes the electron within the lifetime of the fluorescent state. Since the lifetime of the virtual level is very short, a second photon should be available within very short time—hence the high intensity. On the other hand, the pulse energy should be kept prevent thermal or chemical damage to the surrounding tissue. Accordingly, the light is preferably pulsed so that the requirement of high intensity may be fulfilled through a high peak-intensity. A high peak power, but low energy pulse is obtained by using a picosecond, nanosecond or femtosecond laser and by focusing the laser light into the region of the tissue of interest. The combination of focusing and two-photon excitation significantly reduces the risk of damage in the surrounding tissue because the flux of energy needed to achieve excitation exists only at the focal point. Thus, ultraviolet excitation is possible deep within a substance that has a high absorption of ultraviolet, such as the lens. Only red light or infrared radiation with no significant photo-toxic effect exists in front and behind the focus. During treatment, the fluorescence observed along the treatment laser beam in the lens as a result of two-photon processes can be utilized to adjust the focal plane of the treatment laser beam relative to the lens.

Accordingly, in a preferred embodiment the treatment laser beam originates from a treatment laser system comprising at least one ultra fast laser to enable multi-photon effect, such as two-photon effect. Said treatment laser system emitting light at substantially 800 nm, preferably 1030 nm. Preferably the treatment laser system emits laser light in the wavelength range 200-1500 nm, preferably in the range 300-550 nm, in the range 550-700 nm, in the range 700-1000 nm, in the range 1000-1500 nm. In a preferred embodiment the treatment laser beam originates from a Titanium-sapphire laser emitting at 800 nm or a band or line within ±300 nm of 800 nm.

Secondly, the treatment laser beam is preferably pulsing with a pulse width shorter than substantially 60 picoseconds, more preferably with a pulse width shorter than substantially 30 picoseconds, with a pulse width shorter than substantially 10 picoseconds, with a pulse width shorter than substantially 1 picosecond, with a pulse width shorter than substantially 500 femtoseconds, with a pulse width shorter than substantially 200 femtoseconds, with a pulse width shorter than substantially 100 femtoseconds, with a pulse width shorter than substantially 50 femtoseconds, with a pulse width shorter than substantially 5 femtoseconds.

Thirdly, the pulsing of said treatment laser beam preferably comprises pulsing with a pulse energy lower than substantially 200 micro-joules, more preferably substantially 100 micro-joules, substantially 50 micro-joules, substantially 25 micro-joules, substantially 10 micro-joules, or substantially 3 micro-joules.

Fourthly, the treatment laser beam is preferably focused to a spot of with a diameter of substantially 100 microns, more preferably 50 microns, 20 substantially microns, substantially 10 microns, substantially 5 microns, or substantially 1 micron.

Fifthly, the pulse energy density of the treatment laser beam is preferably lower than substantially 1 Joule per square centimeter, lower than substantially 500 milli-Joules per square centimeter, lower than substantially 250 milli-Joules per square centimeter, lower than substantially 100 milli-Joules per square centimeter, lower than substantially 50 milli-Joules per square centimeter, lower than substantially 25 milli-Joules per square centimeter, lower than substantially 10 milli-Joules per square centimeter.

Commonly it is not sufficient to photomanipulate the lens in one position only. Accordingly, in a preferred embodiment of the invention the focus of the laser beam is scanned so as to treat at least one predefined volume, said volume being of a size enabling selective targeting of the lens substance and its sub-regions without damaging adjacent healthy or unhealthy tissue. Preferably the size of the said volume has a cross-section seen from the instrument corresponds to the entire lens or specific parts thereof, or up to about 100 square millimeters, 10 square millimeters, 1 square millimeters, more preferably op to about 0.6 square millimeters, up to about 0.3 square millimeters, up to about 0.1 square millimeters, up to about 0.01 square millimeters, up to about 1000 square microns, up to about 100 square microns, up to about 10 square microns, up to about 1 square microns.

Light Source

The light source preferably comprises compact a laser source delivering short, tunable pulses of laser light with an adjustable delay of very short duration between consecutive pulses. Said duration is preferably shorter than the decay time of the excited compounds, each in a desired spectral range, for sequential two-photon excitation of lens proteins. The availability of closely spaced trains of light pulses is intended to elicit subtle localized effects that will induce cleavage of lens protein cross-links by sequential excitation of molecular bonds in excitation steps that use pulses too weak to induce cleavage in a single excitation step. Single pulses for standard multi-photon excitation will also be available.

One possible solution is to build the light source as a tuneable optical parametric oscillator (OPO) pumped by a frequency-doubled titanium-sapphire laser that in turn is pumped by a continuous-wave frequency-doubled diode-pumped Nd:YAG or Nd:YVO$_4$ laser. The tuneable frequency-doubled titanium-sapphire laser provides an excitation photon in the blue to near UV-wavelength range (~350-450 nm).

Accordingly, in a preferred embodiment of the invention, the treatment laser system comprises a tuneable optical parametric oscillator pumped by a frequency doubled titanium-sapphire laser, wherein said frequency doubled titanium-sapphire laser is in turn pumped by a continuous-wave frequency doubled diode-pumped laser.

Another possible solution is to build the light source as a tuneable optical parametric oscillator (OPO) pumped by a titanium-sapphire laser, wherein said titanium-sapphire laser is in turn pumped by a diode laser. The tuneable titanium-sapphire laser can provide an excitation photon in the range 650-1100 nm. The OPO allows the breaking of this photon into two, one at a higher wavelength than half the titanium-sapphire photon (the signal pulse), and the other of lower wavelength that half the titanium-sapphire photon (the idler pulse). A delay of 0 to a few ns is introduced between the two OPO pulses by an adjustable optical delay line. A specification of the exact tuning range for the OPO-pulses requires a detailed calculation of the phase matching conditions with input parameters from the chosen OPO-crystal (e.g. LBO), but a tuning range of about 50 nm can be expected based on information available from previous investigations.

Accordingly, in a preferred embodiment of the invention, the treatment laser system comprises a tuneable optical parametric oscillator pumped by a titanium-sapphire laser, wherein said titanium-sapphire laser is in turn pumped by a diode laser. In a preferred embodiment, the titanium sapphire laser emits light at a wavelength of or close to 800 nm with a repetition rate of either 31 kHz or 275 kHz. The intensity of the titanium sapphire laser beam is in the range 50 mJ/cm$^2$ to 300 mJ/cm$^2$, and the pulse length below 250 femto-seconds.

In another preferred embodiment, the treatment laser system comprises a tuneable optical parametric oscillator, a titanium-sapphire laser, and a diode laser, wherein said optical parametric oscillator is pumped by said titanium-sapphire laser which is in turn pumped by said diode laser.

In yet another preferred embodiment, the treatment laser system comprises a photonic crystal fiber, where said fiber is preferably pumped by a diode laser.

Scanning of beam relative to lens.

During treatment of the lens, the laser beam may be scanned over at least a part of the lens. The scanning can be performed using various scanning patterns, such as meander scan, discontinous line-by-line scan, a continuous line-by-line scan spiral scan, and/or circular scan. Furthermore, the scan velocity can be adjusted between scans or during a scan. The scan may furthermore be repeated one or several times. A preferred scan velocity is between 1 and 1000 microns per second, more preferably between 10 and 500 microns per second, even more preferably between 50 and 250 microns per second, more preferably between 75 and 125 microns per second.

In some embodiments, the volume of the lens that is treated by the laser beams is 1 millimeter times 1 millimeter times 1 millimeter.

The means for scanning a beam over an object may comprise the means known to a person skilled in the art.

Immobilization

The human eye exhibits micro-movements with a frequency in the order 10 Hz. These micro-movements are involuntary and it is therefore not possible for a subject receiving photomanipulation to suppress theses movements by will. In one preferred embodiment of the present invention spatially accurate photomanipulation is obtained by mechanically immobilizing the living eye, wholly or partly, during treatment, by mechanical contact with the surface of the eye or by mechanical contact to a contact lens mounted on the eye.

Furthermore, this mechanical immobilization preferably further comprises a fluid interface in the said mechanical contact, as well known in the art, and/or an application of suction to reinforce the said mechanical contact also well known in the art.

Movement and Orientation Tracking

Tracking of eye movements and/orientation is an alternative or supplement to immobilization of the eye rendering a high potential for accuracy. Specifically if coupled to response system which provides real-time beam adjustment, so that eye movements are nullified relative to the system.

Accordingly, a preferred embodiment of the invention comprises a method of tracking the movement of the eye by imaging of the eye on at least one light detector.

Preferably the said at least one of the said light detector(s) comprises a camera and preferably the movement of the eye is found by tracking reference points in the eye. To obtain even higher accuracy the said light detectors may be spatially separated so a 3D perspective may be calculated. Accordingly, it is preferred that each light detector views the eye from different angles.

In another preferred embodiment of eye tracking according to the invention, the orientation of an eye in space is monitored by simultaneously monitoring the surface or anterior part of the eye and the fundus (posterior inside of the eye) and calculating the orientation of the eye in space.

Conditioning and Administration of Adjuvant Pharmaceuticals

To make the lens more susceptible to photomanipulation and/or more susceptible to remove bi-products of the photomanipulation, it is for some applications advantageous to condition the eye prior, during, or post photomanipulation or assessment. Accordingly, in a preferred embodiment the invention comprises a method for conditioning the eye prior to treatment, during treatment, post treatment, prior to assessment, during assessment or post assessment by applying at least on of the following: heat, cold and magnetic field.

Similarly, in another preferred embodiment the invention comprises the administration of adjuvant pharmaceuticals. Preferably, these pharmaceuticals quench free radicals in the eye. Such free radicals may arise as an undesired bi-product of the photomanipulation and are preferably disposed by means other than interaction with healthy tissue.

DETAILED DESCRIPTION OF THE DRAWINGS

The method and system according to the present invention are illustrated via non-limiting examples in FIGS. 1-6.

FIG. 1 shows an example of a system (1) according to the invention suitable for non- or minimally disruptive photomanipulation of the lens (2) and/or its constituents collectively or selectively of an animal or human eye (3), comprising:
  e) a treatment laser system (4) for emitting at least one treatment laser beam (5);
  f) focusing means (6) for focusing said treatment laser beam (5) into a selected part of the lens (7) and/or its constituents collectively or selectively where treatment is intended to occur;
  g) means (8) for measuring one or more types of radiation from the said selected part;
  h) means (9) for processing the said one or more type of radiation from the said selected part;
  i) means (10) for adjusting, based on at least part of the output of the means for processing.

Figure 2:
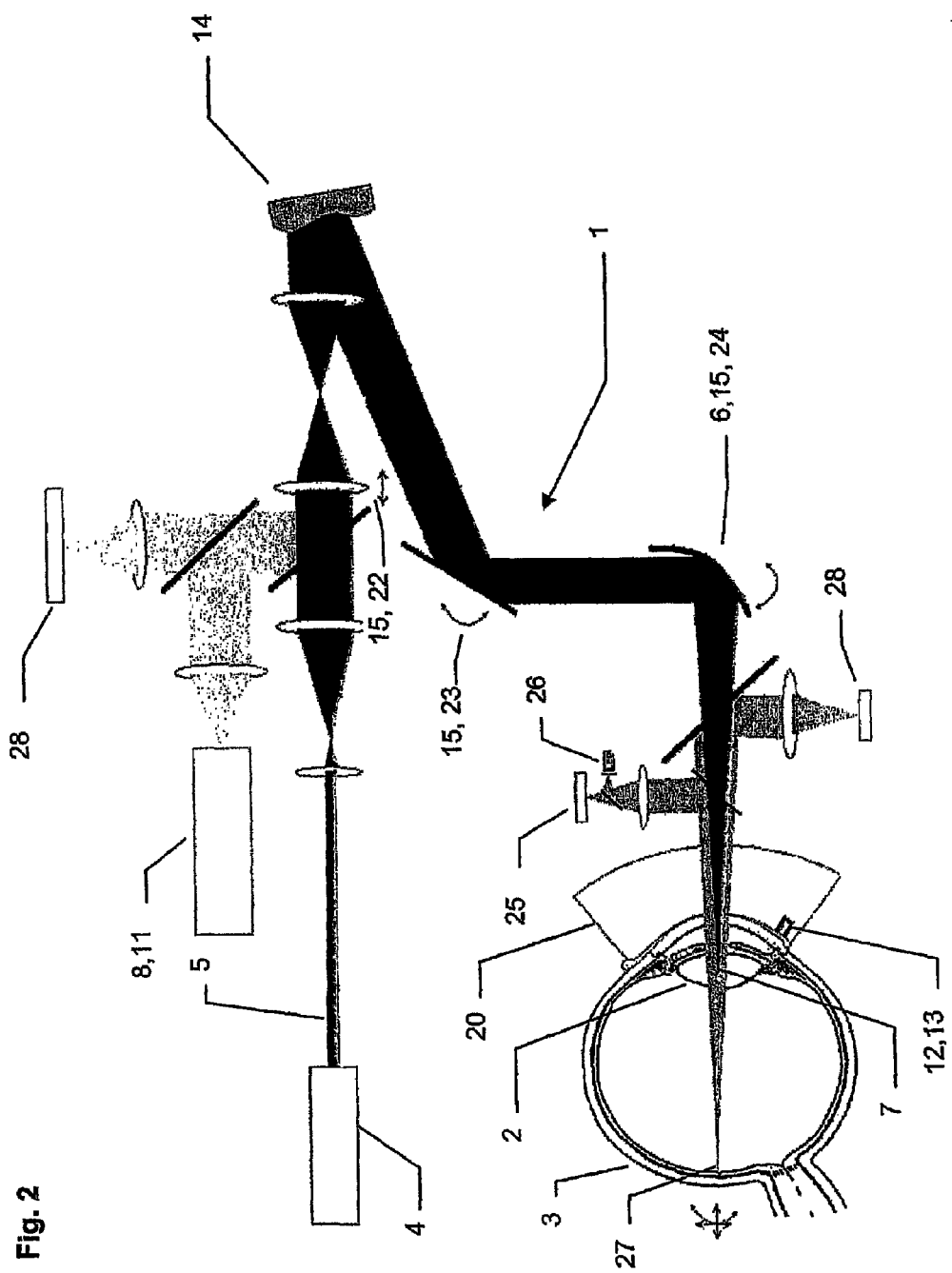
FIG. 2 shows a schematic overview of a system according to the invention including several features such as adaptive optics.

FIG. 2 shows another example of a system according to the present invention further comprising:
  a) means (11) for determining the optical signature of the said selected part, such as a time-resolved spectrometer,
  b) means (12, 13) for detecting acoustic effects where the sensor has been placed in mechanical contact with the eye,
  c) adaptive optics (14) here exemplified by a deformable mirror,
  d) means (15) for scanning the focus of said treatment laser beam at least one predefined volume, where the depth of the focus is scanning by moving the lens (22) in the setup, and the position is scanned by moving the plane mirror (23) and the curved mirror (24),
  e) means for imaging the iris or movements thereof (25),
  f) means for providing a fixation target here shown as LED (26), said target being projected (27) onto the retina,
  g) means for imaging the fundus or movements thereof (27),
  h) and means for imaging the target (28).

Figure 3:
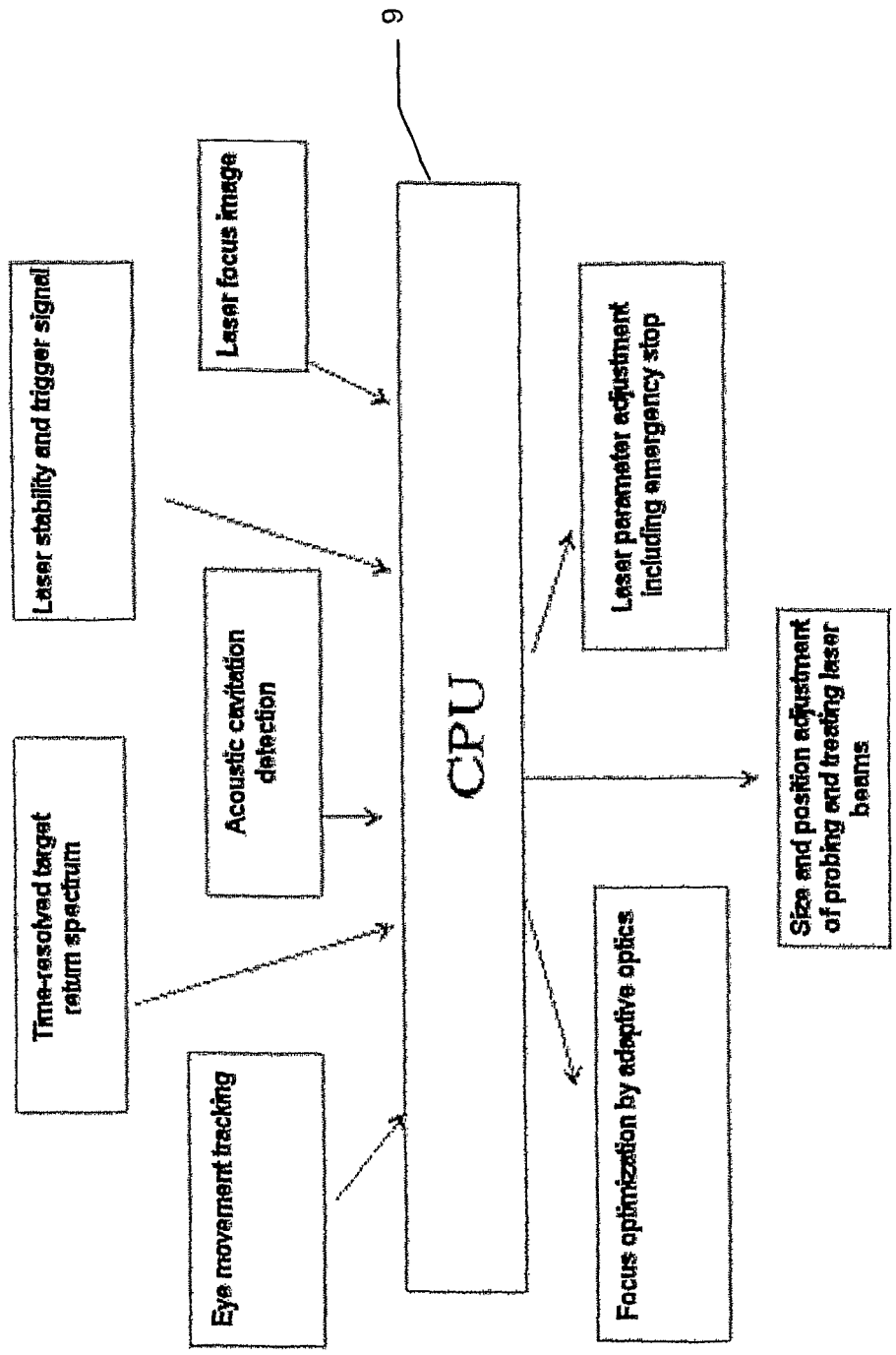
FIG. 3 shows several of the different forms of information the means for processing may receive as input and provide as output.

FIG. 3 shows the one example of information flow to and from the means for processing (9). Although sketched as a single box the invention is not limited to having the processing means confined to a single unit. Instead, the processing may be performed by several computers and/or dedicated hardware units. Some processes may also be analysed manually.

Figure 4:
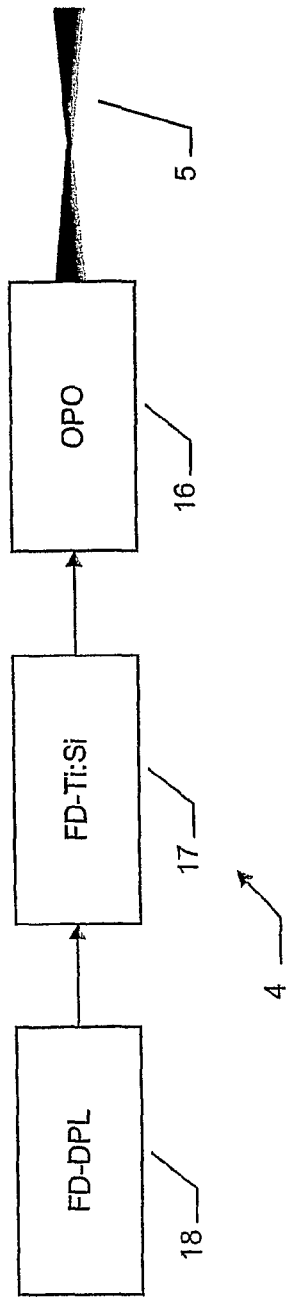
FIG. 4 shows a suitable laser system.

FIG. 4 shows an example of a suitable treatment laser system (4) comprising a tuneable optical parametric oscillator (16), a frequency doubled titanium-sapphire laser (17), and a continuous-wave frequency doubled diode-pumped laser (18), wherein said optical parametric oscillator (16) is pumped by said frequency doubled titanium-sapphire laser (17) which is in turn pumped by said continuous-wave frequency doubled diode-pumped laser (18).

Figure 5:
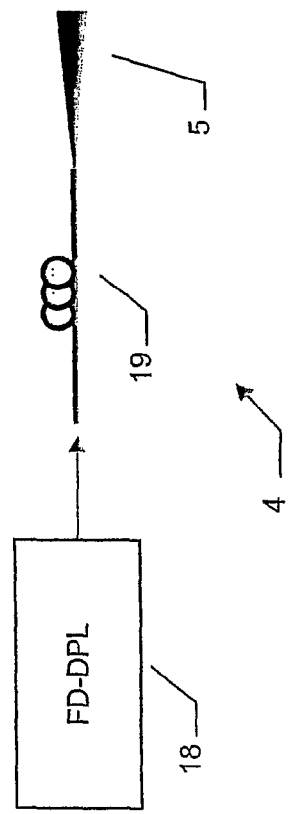
FIG. 5 shows a suitable laser system.

FIG. 5 shows an example of a suitable treatment laser system (4) comprising a photonic crystal fiber (19) and a continuous-wave frequency-doubled diode-pumped laser (18), wherein said optical parametric oscillator is pumped by said frequency doubled titanium-sapphire laser which is in turn pumped by said continuous-wave frequency doubled diode-pumped laser.

Figure 6:
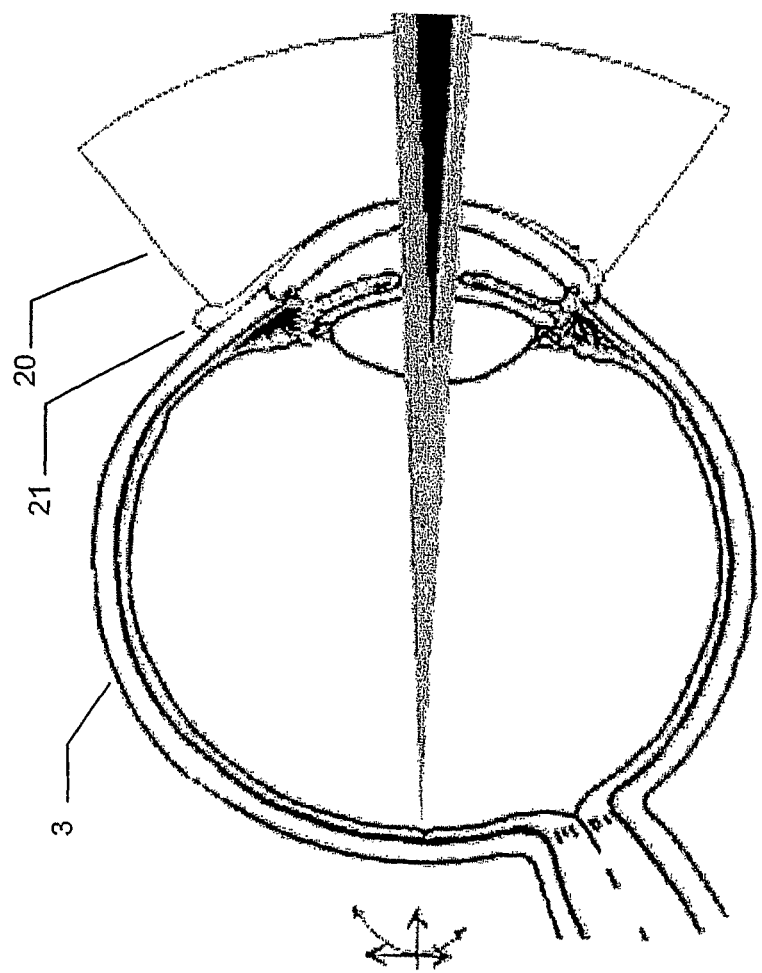
FIG. 6 shows an eye on which a contact lens is attached as well as a fluid connection between the eye and the said contact lens.

FIG. 6 shows one aspect of the invention where the living eye (3) is mechanically immobilizing wholly or partly, during treatment, by means for mechanical contact to a contact lens (20) mounted on the said eye (3). Furthermore, to improve the connection fluid interface (21) is utilized in said means for mechanical contact.

EXAMPLES

The following example provides further details of a system according to the invention such as shown in FIG. 1. The present example a system for lens phototherapy system uses one or more sources of light to aim and photomanipulate a selected volume of the lens of the human or animal eye. A specific embodiment of the invention uses an 800 nm titanium-sapphire laser at 275 kHz repetition rate, 238 femtossecond pulse duration, pulse energy 0.04 µJ, peak power 0.18 MW, and transverse target area radius of 10-200 µm. After acquiring a target area in the lens by the using of classical imaging optics, which may include slit-beam illumination and/or Scheimpflug real-time photography (not shown), a laser pulse or pulse train is applied in incremental energy steps to arouse a succession of events in the target volume, the nature of these events being detectable by the optical signature recorded by the spectrometer. These events include but are not limited to backscatter, fluorescence, Raman scatter and bremsstrahlung from plasma formation. By using one of more of these return signals from the tissues while imaging the shape and extent of the target volume, an adaptive optics feed-back loop enables control of a flexible mirror and optimized focusing of the laser energy. By rapid focusing of the incoming beam and adjustment of the energy required to produce fluorescence or any other measure of tissue response alone or in combination, the sub-threshold probing light pulse is followed by a supra-threshold laser pulse that achieves the desired optical endpoint, e.g. bleaching of the fluorophore, a change in scatter, refractive index, or transparency. Subsequently, the instrument's focus is moved through a series of target volume locations, thus enabling the entire lens or a predefined sub-volume thereof to be photomanipulated. A further embodiment of the invention uses a 1030 nm crystal fiber laser to evoke two-photon fluorescence, observed through a barrier filter or by means of a spectrometer to cover a bandwidth of approximately 530 to 630 micrometers, and, closely thereafter, increase the energy gradually, pulse-by-pulse, until three-photon fluorescence of approximate bandwidth 320-420 nm, and subsequent decay of the fluorescence of the target area, this being indicative of multi-photon bleaching or other optical change having occurred within the tissue at the target site, provided that no movement of the eye has taken place. The position of the target volume within the lens is being constantly monitored by real-time analysis of the images of the fundus (posterior inside of the eye) and structures of the anterior end of the eye, notably the iris, the response time of the eye position-control system being less than 0.1 second and the time-course of target acquisition, probing and treatment being completed within 0.1 second.

REFERENCES

Birgit Sander, Larsen M: Photochemical Modulation of Non-Enzymatic Glucosylation. European Association for the Study of Diabetic Eye Complications. London, 9. September 1991.
Birgit Sander, Larsen M: Photochemical bleaching of fluorescent glycosylation products. VI Meeting of the Int. Soc. of Ocular Fluorophotometry, Bruxelles, 27. maj 1992.
Sander B, Larsen M: Photochemical bleaching of fluorescent glycosylation products. Int Opthalmol 18:195-198, 1995.

What is claimed is:

1. A system for non- or minimally disruptive photomanipulation of the lens of an animal or human eye, comprising:
   a) a treatment laser system for emitting at least one treatment laser beam with wavelength of the light in the range of 700-1000 nm or in the range of 1000-1500 nm;
   b) focusing means for focusing said treatment laser beam into a selected part of the lens where treatment is intended to occur;
   c) means for pulsing of said treatment laser beam;
   d) means for measuring one or more types of radiation from the said selected part;
   e) means for processing the said one or more type of radiation from the said selected part;
   f) means for adjusting, based on at least part of the output of the means for processing, at least one of the parameters for the said treatment laser beam: focus, intensity, wavelength, pulse length, repetition frequency, and pulse train length of said treatment laser beam.

2. A system of claim 1, furthermore comprising means for scanning the treatment laser beam relative to the lens and wherein part f) furthermore comprises means for adjusting, based on at least part of the output of the means for processing, at least one of the parameters: the scan velocity, the size of scanned volume, the scan repetitions, and the scan pattern.

3. The system of claim 1, comprising means for emitting non-manipulative intensity directed to the said selected part either from the said treatment laser system or from secondary means for emitting radiation.

4. The system of claim 3, further comprising second means for measuring and/or processing one or more types of radiation, caused by the interaction between the said selected part and the said non-manipulative intensity.

5. The system of claim 4, where the output from the said means for processing are used to obtain input to said means for adjusting at least one of the said parameters for the said treatment laser beam or to determine if manipulative intensity should be applied.

6. The system of claim 1, comprising means for determining the optical signature of the said selected part comprising at least one of the following: transient characteristics arising as an effect of the said pulsing of the said treatment laser beam or any characteristic that can be recorded using steady-state or time-resolved spectroscopy, Raman spectroscopy, photon-correlation spectroscopy, fluorescence spectroscopy and/or phosphorescence spectroscopy.

7. The system of claim 1, where the said means for measuring comprises means for detecting acoustic effects.

8. The system of claim 7, where the said means for detecting acoustic effects comprises one or more non-contact sensor(s) and/or one or more acoustic sensor(s) placed in direct or indirect contact with the eye or adjacent tissue.

9. The system of claim 1, where the said means for measurement, processing and adjustment form a feed-back loop.

10. The system of claim 1, wherein the said measurement, processing of resulting data, said adjustment(s), and renewed irradiation of the said selected part occurs within a time period which is less than the spontaneous movements of the eyes (saccades).

11. The system of claim 1, where the said treatment laser beam and/or any secondary source of radiation is focused using adaptive optics.

12. The system of claim 11, where the adaptive optics form a feedback loop.

13. The system of claim 11, where the adaptive optics is guided by radiation caused by the said treatment laser beam or a said secondary source of radiation.

14. The system of claim 1, where the said means for measuring radiation comprises means for detection of at least one of the following: fluorescence, scatter, Raman scatter, reflection, phosphorescence, and bremsstrahlung.

15. The system of claim 1, where the said means for measurement comprises means for measuring the spectral distribution of the said radiation and/or means for temporally and/or spectrally resolved analysis.

16. The system of claim 1, where said treatment laser beam is adjusted to obtain bleaching, color change, deaggregation of lens components, depolymerization of lens proteins or other constituents of the lens, or resolubilization of lens proteins or other constituents of the lens while avoiding or minimizing cavitation, mechanical effects, acoustic effects, and/or thermal effects on molecules, components, or cells that do not form a target for treatment or are outside said selected area.

17. The system of claim 1, where said treatment laser beam is adjusted to obtain molecular cleavage of specific larger molecules or macromolecular adducts without damage to healthy lens proteins, cell membranes or other healthy components of the lens, and further avoiding or minimizing cavitation, mechanical effects, acoustic effects, and/or thermal effects on molecules, components, or cells that do not form a target for treatment or are outside said selected area.

18. The system of claim 1, where said treatment laser system comprises at least one ultra fast laser to enable multi-photon effect.

19. The system of claim 1, where said pulsing comprises pulsing the treatment laser beam with a pulse width shorter than 1 picosecond.

20. The system of claim 1, where said pulsing comprises pulsing the treatment laser beam with pulse energy lower than 200 micro-joules.

21. The system of claim 1, further comprising means for scanning the focus of said treatment laser beam into at least one predefined volume, said volume being of a size enabling selective targeting of the lens substance and its sub-regions without damaging adjacent healthy or unhealthy tissue.

22. A system for treating a person or animal in need of treatment for cataract, pre-cataract or presbyopia by non- or minimally disruptive photomanipulation of the lens of an animal or human eye, comprising:
   a) means for focusing a treatment laser beam into a selected part of the said lens where treatment is intended to occur, said treatment laser beam with wavelength of the light in the range of 700-1000 nm or in the range of 1000-1500 nm;
   b) means for pulsing of said treatment laser beam;
   c) means for measuring one or more types of radiation from the said selected part;
   d) means for processing the said one or more type of radiation from the said selected part;
   e) means for adjusting at least one of the parameters for the said treatment laser beam: focus, intensity, wavelength, pulse length, repetition frequency, and pulse train length of said treatment laser beam,
   thereby optimally photobleaching said cataract, pre-cataract or presbyopia and thus treating the disease.

23. A method for non- or minimally disruptive photomanipulation of the lens and/or its constituents collectively or selectively of an animal or human eye, comprising:
   a) focusing a treatment laser beam into a selected part of the lens and/or its constituents collectively or selectively where treatment is intended to occur;
   b) pulsing of said treatment laser beam;
   c) scanning the treatment laser beam relative to the lens;
   d) measuring one or more types of radiation from the said selected part and utilizing this measurement to decide to stop the said treatment laser beam or to adjust at least one of the parameters: focus, intensity, wavelength, pulse length, repetition frequency, and pulse train length of said treatment laser beam and utilizing the measurement to decide to adjust at least one of the parameters: scan velocity, size of scanned volume, scan repetitions, and scan pattern.

24. The method of claim 23, where at least one of said types of radiation arises due to said treatment laser beam and/or due to a secondary source of radiation, such as a laser.

25. The method of claim 23, further comprising an initialization phase prior to steps a)-c) where non-manipulative intensity is directed to the said selected part and one or more types of radiation, caused by the interaction between the said part and the said non-manipulative intensity are measured and utilizing this measurement to decide not to photomanipulate said selected part or decide to proceed with photomanipulation.

26. The method of claim 25, where said initialization phase is further utilized to adjust at least one of the following: focus, intensity, wavelength, pulse length, repetition frequency, pulse train length, scan velocity, size of scanned volume, scan repetitions, and scan pattern of said treatment laser beam.

27. The method of claim 23, further comprising an assessment phase after application of the said treatment laser beam where non-manipulative intensity is directed to the said selected part and measuring one or more types of radiation caused by the interaction between the said part and the said non-manipulative intensity and utilizing this measurement to decide to stop further treatment of said part or to resume treatment with or without adjustment of at least one of the following: focus, intensity, wavelength, pulse length, repetition frequency, pulse train length, scan velocity, size of scanned volume, scan repetitions, and scan pattern of said treatment laser beam.

28. The method of claim 23, where the said measurement involves determining the optical signature of the said selected part comprising at least one of the following: transient characteristics arising as an effect of the treatment pulse or any characteristic that can be recorded using steady-state or time-resolved spectroscopy, Raman spectroscopy, photon-correlation spectroscopy, fluorescence spectroscopy and/or phosphorescence spectroscopy.

29. The method of claim 23, where the said measurement involves detection of acoustic effects recorded using non-contact sensor(s) and/or an acoustic sensor placed in direct contact with the eye or adjacent tissue.

30. The method of claim 23, where the said measurement, analysis and adjustment form a feed-back loop.

31. A method of claim 23, wherein the said measurement, processing of resulting data, said adjustment(s), and renewed irradiation of the said selected part occurs within a time period which is substantially smaller than the spontaneous movements of the eyes (saccades).

32. A method of claim 23, wherein fluorescence observed along the treatment laser beam path in the lens due to two-photon processes are used to adjust the focal plane relative to the lens.

33. The method of claim 23, where a procedure is performed comprising the following steps:
   a) photomanipulating said selected part
   b) detection radiation from the said selected part
   c) gradually increasing energy of said photomanipulation
   d) registering when said radiation is below a defined threshold.

34. The method of claim 23, further comprising a verification of efficiency by measurement of radiation due to a non-manipulative intensity directed to the said selected part.

35. The method of claim 23, further comprising comparing values of said radiation obtained prior to treatment with the data obtained from said verification.

36. The method of claim 23, where the treatment laser beam and/or any secondary source of radiation is focused using adaptive optics, said adaptive optics further comprises the use of a deformable minor and/or the use of a Hartmann-Schack sensor.

37. The method of claim 36, where the adaptive optics form a feedback loop.

38. The method of claim 37, where the adaptive optics is guided by radiation caused by the said treatment laser beam or a said secondary source of radiation.

39. The method of claim 23, where the said radiation comprises at least one of the following: fluorescence, scatter, Raman scatter, reflection, phosphorescence, and bremsstrahlung.

40. The method of claim 23, where the said measurement comprises measuring the spectral distribution of the said radiation.

41. The method of claim 23, where said treatment laser beam is adjusted to obtain bleaching, color change, deaggregation of lens components, depolymerization of lens proteins or other constituents of the lens, or resolubilization of lens proteins or other constituents of the lens while avoiding or minimizing cavitation, mechanical effects, acoustic effects, and/or thermal effects on molecules, components, or cells that do not form a target for treatment or are outside said selected area.

42. The method of claim 23, where said treatment laser beam is adjusted to obtain molecular cleavage of specific larger molecules or macromolecular adducts, for instance lens proteins or lens protein cross-links, without damage to healthy lens proteins, cell membranes or other healthy components of the lens, and further avoiding or minimizing cavitation, mechanical effects, acoustic effects, and/or thermal effects on molecules, components, or cells that do not form a target for treatment or are outside said selected area.

43. The method of claim 42, where the said radiation is fluorescence while minimizing or preventing the increase in scattering.

44. The method of claim 23, where said treatment laser beam originates from a treatment laser system comprising at least one ultra fast laser to enable multi-photon effect, such as two-photon effect.

45. The method of claim 23, where said pulsing comprises pulsing the treatment laser beam with a pulse width shorter than 60 picoseconds.

46. A method of claim 23, where said pulsing comprises pulsing the treatment laser beam with pulse energy density lower than substantially 1 Joule per square centimeter.

47. The method of claim 23, where the focus of the laser beam is scanned so as to treat at least one predefined volume, said volume being of a size enabling selective targeting of the lens substance and its sub-regions without damaging adjacent healthy or unhealthy tissue.

48. A method of treating a person or animal in need of treatment for cataract, pre-cataract or presbyopia by non- or minimally disruptive photomanipulation of the lens and/or its constituents collectively or selectively of an animal or human eye, comprising:
  a) focusing a treatment laser beam into a selected part of the lens and/or its constituents collectively or selectively where treatment is intended to occur;
  b) pulsing of said treatment laser beam;
  c) scanning the treatment laser beam relative to the lens;
  d) measuring one or more types of radiation from the said selected part and utilizing this measurement to decide to stop the said treatment laser beam or to adjust at least one of the parameters: focus, intensity, wavelength, pulse length, repetition frequency, and pulse train length of said treatment laser beam;
  thereby photobleaching said cataract, pre-cataract or presbyopia and utilizing the measurement to decide to adjust at least one of the parameters: scan velocity, size of scanned volume, scan repetitions, and scan pattern and thus treating the disease.

49. The method of claim 48, wherein adjuvant pharmaceuticals are administered.

50. The method of claim 49, wherein said pharmaceuticals quench free radicals in the eye.

* * * * *